United States Patent
Bander

(10) Patent No.: US 6,299,598 B1
(45) Date of Patent: *Oct. 9, 2001

(54) DRAINAGE CATHETER

(75) Inventor: Neil H. Bander, Chappaqua, NY (US)

(73) Assignee: Cook Urological, Incorporated, Spencer, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/020,593

(22) Filed: Feb. 4, 1998

Related U.S. Application Data

(60) Provisional application No. 60/037,791, filed on Feb. 4, 1997.

(51) Int. Cl.$^7$ ................................ A61M 29/00

(52) U.S. Cl. ...................................... 604/101.03

(58) Field of Search ................. 604/96, 101, 100, 604/102, 264, 278, 280, 283, 327, 328, 355, 912, 915, 919, 921, 101.01, 101.03, 101.05, 102.01, 102.03

(56) References Cited

U.S. PATENT DOCUMENTS

| | | | |
|---|---|---|---|
| 2,642,874 | | 6/1953 | Keeling . |
| 2,799,273 | * | 7/1957 | Oddo ................................ 604/101 |
| 2,936,760 | * | 5/1960 | Gants ................................ 604/101 |
| 4,456,011 | * | 6/1984 | Warnecke .......................... 604/101 |
| 4,634,435 | * | 1/1987 | Ingraham .......................... 604/101 |
| 4,636,195 | * | 1/1987 | Wolinsky .......................... 604/101 |
| 4,660,560 | * | 4/1987 | Klein ................................ 604/101 |
| 4,705,502 | * | 11/1987 | Patel ................................. 604/49 |
| 4,723,946 | | 2/1988 | Kay . |
| 4,781,677 | * | 11/1988 | Wlicox .............................. 604/28 |
| 4,946,449 | * | 8/1990 | Davis, Jr. .......................... 604/34 |
| 4,976,692 | * | 12/1990 | Atad .................................. 604/101 |
| 5,112,306 | * | 5/1992 | Burton et al. ..................... 604/101 |
| 5,188,595 | * | 2/1993 | Jacobi ............................... 604/101 |
| 5,328,470 | * | 7/1994 | Nabel et al. ...................... 604/101 |
| 5,411,479 | * | 5/1995 | Bodden ............................. 604/98 |
| 5,419,763 | * | 5/1995 | Hildebrand ....................... 604/54 |
| 5,462,529 | * | 10/1995 | Simpson et al. ................. 604/101 |
| 5,505,701 | * | 4/1996 | De Lomana ..................... 604/102 |
| 5,540,701 | | 7/1996 | Sharkey et al. . |
| 5,665,063 | * | 9/1997 | Roth et al. ....................... 604/101 |
| 5,674,198 | * | 10/1997 | Leone ............................... 604/101 |
| 5,772,632 | * | 6/1998 | Forman ............................ 604/101 |
| 5,836,967 | * | 11/1998 | Schneider ........................ 604/101 |
| 5,947,977 | * | 9/1999 | Slepian et al. .................. 604/101 |
| 6,007,521 | | 12/1999 | Bidwell et al. . |

* cited by examiner

Primary Examiner—Sharon Kennedy
(74) Attorney, Agent, or Firm—James B. Hunt

(57) ABSTRACT

A suprapubic drainage catheter (10) for draining the bladder and maintaining the patency of the urethra of a patient following a radical prostatectomy. The catheter includes an elongated member (11) having a drainage passage (12) extending longitudinally therein and a plurality of drainage ports (21) in a drainage portion (14) thereof for providing external access for the drainage passage in the bladder of the patient. First and second retention balloons (17, 18) are connected with the elongated member and positioned distally and proximally of the drainage ports, respectively. The elongated member also includes first and second inflation passages (26, 27) for individual and independent inflation and deflation of the retention balloons. One-way connector valves (32, 33) are positioned at the proximal end of the catheter for controlling inflation and deflation of the balloons via the inflation passages. The elongated member also includes a proximal portion (15) that extends through the percutaneous access site (30) for connection of a urine collection bag (not shown) to the drainage passage and further includes a distal portion (13) that extends from the bladder into the urethra through the anastomotic site (20) to maintain the patency of the urethra thereat.

19 Claims, 2 Drawing Sheets

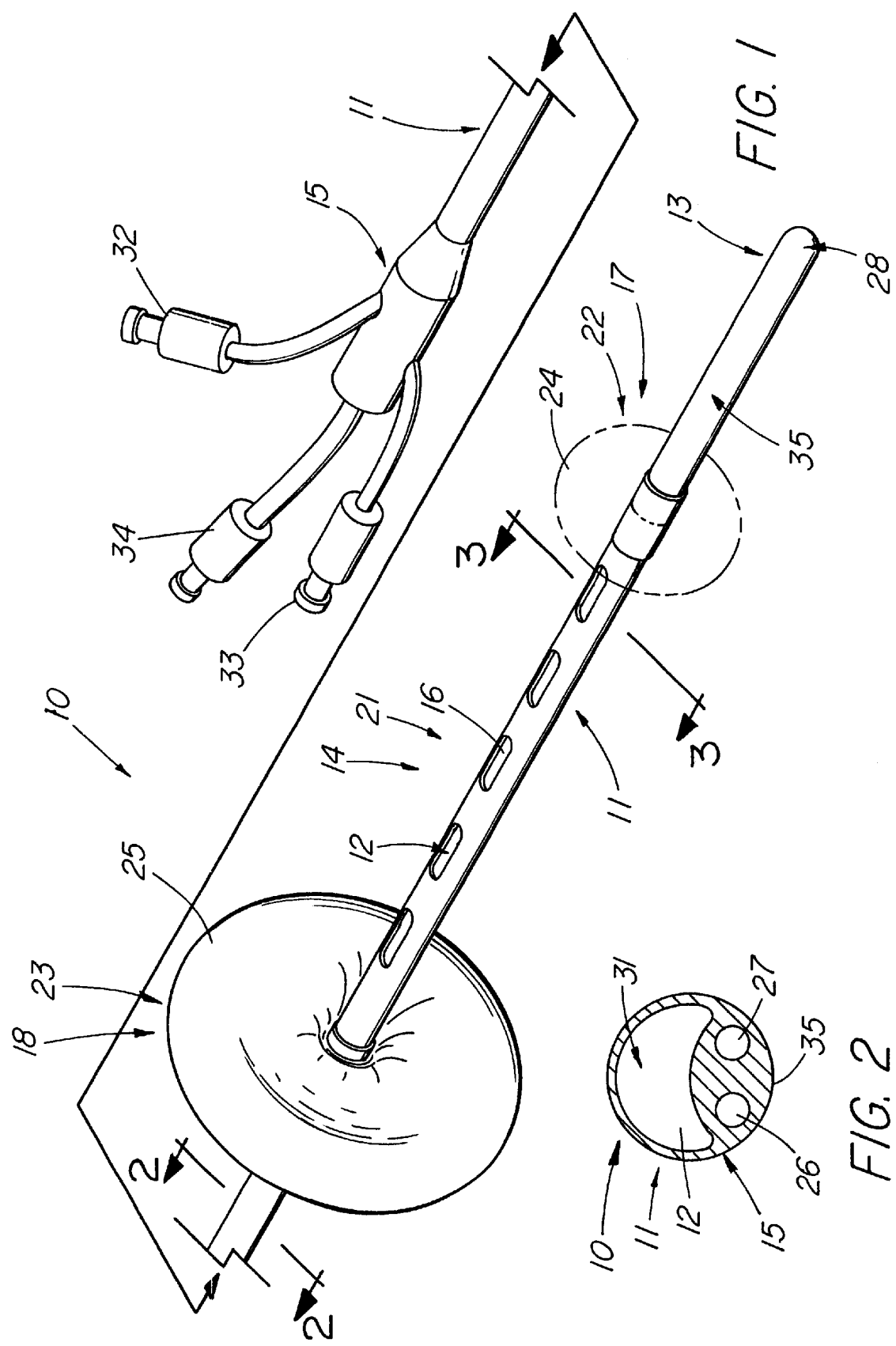

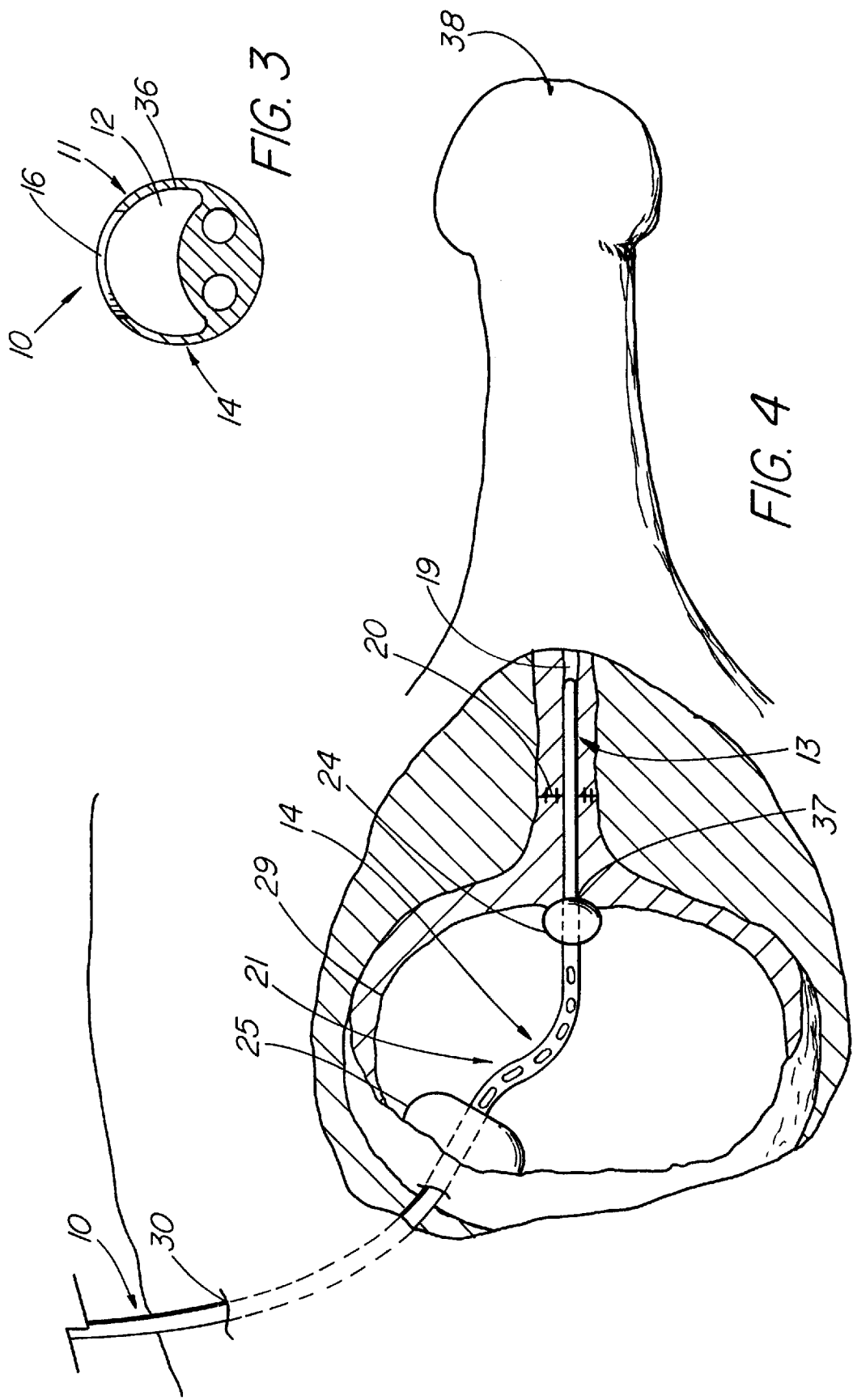

DRAINAGE CATHETER

CROSS-REFERENCE TO RELATED APPLICATIONS

This application claims priority of provisional application Ser. No. 60/037,791 filed Feb. 4, 1997.

TECHNICAL FIELD

The invention relates generally to a medical device and, in particular, to a drainage catheter.

BACKGROUND OF THE INVENTION

A radical prostatectomy can be a very difficult procedure because the surgeon cannot fully visualize the surgical site and work within the tight anatomical constraints. Complications from surgery can include impotence and incontinence due to sphincter damage. After the prostate has been excised, the urethra must be reconstructed to restore normal urinary function to the patient. Typically, the surgeon sutures the transected end of the urethral stump to the bladder neck. Occasionally, surgical complications occur at the anastomotic site such as the leakage of urine or, formation of strictures. The vulnerability of the site and the need to keep the lumen patent necessitates a means of support during the healing phase to achieve good anastomosis of the reconstructed urethra.

Radical prostatectomy patients require urinary drainage by an indwelling catheter following the procedure. The standard procedure for prostatectomy patients is to place a Foley drainage catheter at the time of surgery to be left in place for two to three weeks (healing period). While it is placed for drainage, the catheter also serves to keep the anastomotic site patent during the healing process. Although transurethral catheters can maintain urethral patency while providing post-surgical drainage of the bladder, there are disadvantages associated with their use. They are uncomfortable, resulting in a tendency for some patients to pull on the end of the catheter, which may dislodge it from the bladder. Occasionally, the retention balloon will deflate, permitting the catheter to migrate past the anastomotic site and out of the bladder. Another potential complication is that transurethral drainage catheters can become a pathway for pathogens and organisms that are carried or migrate from the skin surface through the urethra to the anastomotic site and the bladder. This may lead to infection and curtail the healing process. Furthermore, transurethral drainage catheters are not ideal for promoting good anastomosis of the surgical site because movement of the balloon may allow urine to leak around the catheter, which provides a suboptimal environment for healing. Foley catheters have only one or two drainage holes which may easily become obstructed by blood clot(s) resulting in poor or no drainage and anastomotic compromise. If the anastomotic site can be kept relatively dry, the likelihood of a good result is increased. Additionally, accidental jerking or other movement of the catheter can cause trauma to the bladder and/or anastomosis before the healing process is complete.

SUMMARY OF THE INVENTION

The foregoing problems are solved and a technical advance is achieved in an illustrative drainage catheter having an elongated member having a drainage passage with at least on e drainage port positioned between first and second retention members, and a closed-ended distal portion sized and configured for maintaining patency of a vessel in the vicinity of an anastomotic site. In one useful application, the drainage catheter is positioned not only in the bladder, but through the anastomotic site in the urethra as well, of a patient who has undergone a radical prostatectomy or other procedure requiring reconstructs of the bladder-urethral anastomosis. The drainage catheter comprises an elongated member having a drainage lumen passage extending longitudinally within and a drainage portion having at least one drainage port that provides external access for bladder contents via the drainage passage. The elongated member also has a distal segment that is located distal to the drainage port. This distal portion/segment has no drainage port or drainage passage. The distal portion of the elongated member is advantageously positioned through the anastomotic site into the urethra of a patient and to maintain patency of the anastomosis and urethra during the healing process. Furthermore, the distal non-draining portion also advantageously minimizes, if not eliminates, urine collected in the bladder from migrating to the anastomotic site. The closed distal portion also blocks external access of the drainage passage so as to eliminate any urine in the drainage catheter from exiting the distal portion and contacting the anastomotic site.

The drainage catheter further includes a first retention member, preferably an expandable balloon that is connected to the elongated member and positioned distal to the drainage segment. When expanded, this first retention balloon advantageously is positioned at the base of the bladder adjacent the bladder neck to further minimize the migration of urine into the urethra and, more importantly, the anastomotic site. A second retention member, preferably another expandable balloon, is connected to the elongated member and positioned proximal to the drainage segment. This second retention balloon is advantageously expanded in its position at the dome of the bladder and works in cooperation with the first retention balloon to maintain the drainage portion of the catheter in the bladder as well as the distal portion in the patient's urethra.

The elongated member of the drainage catheter also includes a proximal portion that is positioned proximal the drainage port and provides external egress from the drainage passage outside the patient. The first and second retention members can include first and second expandable members that are mechanical in nature, each having a collapsed and an expanded state surrounding the elongated member at opposite sides of the drainage port. In one configuration, the retention members, as previously suggested, include first and second balloons. Accordingly, the elongated member includes at least one inflation passage and, preferably, first and second inflation passages extending longitudinally therein and communicating with the first and second retention balloons, respectively. Separate inflation passages advantageously provide for individual and independent inflation and deflation of the balloons.

To further enhance drainage of urine from the bladder, the drainage portion includes a plurality of drainage ports, each preferably having an elliptical shape for maximizing the flow of urine therethrough. The drainage passage of the elongated member also has a preferred crescent, cross-sectional shape to minimize the collection of pathogens and organisms therein as well as the formation of encrustations.

The distal portion of the elongated member is advantageously sized and configured for maintaining the patency of the urethra in the vicinity of the anastomotic site. To further ease insertion thereof and minimize trauma to surrounding tissue, the distal portion includes an atraumatic end preferably having a hemispherical shape. The elongated member preferably comprises a soft, silicone material. However, to enhance fluoroscopic or radiographic visualization of the catheter, the elongated member includes a radiopaque material. Furthermore, to minimize pathogen and organism growth, the elongated member includes a medicant, such as Rifampin/Minocycline, either singly or in combination with other medicants. Surfactants, coatings, chemical bonding, implantation, imbedding, and encapsulation can be used singly or in combination to deliver advantageously one or more medicants at any desired delivery rate.

BRIEF DESCRIPTION OF THE DRAWING

FIG. 1 depicts an illustrative embodiment of a suprapubic drainage catheter of the present invention;

FIG. 2 depicts an enlarged, cross-sectional view of the proximal portion of the suprapubic drainage catheter of FIG. 1 along the line 2—2;

FIG. 3 depicts an enlarged, cross-sectional view of the suprapubic drainage catheter of FIG. 1 along the line 3—3; and FIG. 4 depicts the drainage catheter of FIG. 1 suprapubically positioned in a patient.

DETAILED DESCRIPTION

FIG. 1 depicts an illustrative embodiment of a suprapubic drainage catheter 10 for percutaneous placement not only in the bladder but, in addition, the urethra of a patient who has undergone a radical prostatectomy or other procedure requiring reconstruction of the bladder-urethral anastomosis. The catheter includes an elongated member 11 of, for example, a tubular medical grade silicone material having a drainage passage 12 extending longitudinally therein. The elongated tubular member includes a drainage portion 14 having at least one drainage port 16 and, preferably, a plurality of drainage ports 21 that provide external access for urine in the bladder to enter the drainage passage and drain therefrom into a urine collection bag attached to the proximal end of the catheter. The position of the drainage portion is maintained in the bladder between the dome and neck thereof via first and second retention members 17 and 18.

The elongated tubular member also includes a distal portion 13 having a closed, atraumatic end 28 for placement in the urethra of a patient and, more particularly, through an anastomotic site in the urethra, which is formed as a result of surgical reconstruction after removing the patient's prostate. The distal portion of the elongated tubular member is imperforate and blocks external egress from the drainage passage to minimize urine from contaminating the anastomotic site. Furthermore, the length of the distal portion is sized so as to remain in the fossa navicularis of the urethra. As a result, the patient's external urethral orifice is maintained in a collapsed or closed state to minimize the migration of pathogens and other infectious organisms from accessing the anastomotic site, which significantly improves the healing process. Furthermore, the distal portion of the drainage catheter is sized and configured for maintaining patency of the urethra in the vicinity of the anastomotic site.

The suprapubic draining catheter also includes first and second retention members 17 and 18 connected with the elongated tubular member and positioned distally and proximally of the drainage ports 21, respectively. The retention members maintain the relative positions of the drainage and distal portions of the drainage catheter in the bladder and urethra of the patient, respectively. Preferably, first and second retention members 17 and 18 are first and second balloons 24 and 25, respectively. The retention members or balloons assume a collapsed state around the elongated tubular member of the catheter for percutaneous insertion of the distal and drainage portions into the urethra and bladder. When the distal portion is positioned in the urethra through the anastomotic site, the retention members are actuated to an expanded state. The retention members 17 and 18 can also be more generally described as first and second expandable members 22 and 23, each having a collapsed and an expanded state. The expandable retention members can be a sleeve of material connected at one end to the external surface of the tubular member. The other end of the sleeve is connected to a rod or stylet that slides in the tubular member to expand and collapse longitudinal strips cut in the sleeve. This mechanically actuated expandable retention member configuration is commonly referred to as a Malincot. Preferably, first and second retention members 17 and 18 or expandable retention members 22 and 23 are balloons 24 and 25, which are individually inflated and expanded through inflation passages extending longitudinally in the elongated tubular member. The inflation passages are terminated at the proximal end of proximal portion 15 via well-known one-way connector valves 32 and 33, commonly referred to as Halkey-Roberts valves. Similarly, drainage passage 12 is terminated at its proximal end with flow-through connector hub 34.

Lastly, elongated tubular member 11 includes a proximal portion 15 that is positioned proximal to the drainage ports 21 and also provides external egress from drainage passage 12 for drainage of fluid from drainage passage 12. In use, connector hub 34 of the catheter is connected to a commercially available urine collection bag. In addition, the one-way connector valves 32 and 33 are connected to a commercially available pump or syringe for individually and independently inflating and deflating retention balloons 24 and 25, respectively.

FIG. 2 depicts an enlarged, cross-sectional view of the proximal portion 15 of suprapubic drainage catheter 10 of FIG. 1 along the line 2—2. This cross-sectional view of elongated tubular member 11 depicts proximal portion 15 with drainage passage 12 and first and second inflation passages 26 and 27 in a preferred side-by-side or adjacent configuration, although a coaxial configuration is contemplated. To minimize collection of pathogens or organisms or the formation of encrustations, drainage passage 12 has a crescent shape 31. Inflation passages 26 and 27 are of a circular shape. For ease of manufacture, all three passages extend the entire length of elongated tubular member 11 and are closed at atraumatic distal end 28, which preferably has a hemispherical shape.

Returning the reader's attention to FIG. 1, first retention balloon 24 is positioned distal of drainage ports 21 and, preferably, 5 to 8 cm proximal to the atraumatic distal end 28. The retention balloon is toroidal or doughnut shaped and preferably displaces 5 cc of volume when inflated. However, the volume of the retention balloon can range from 5 cc to 50 cc, depending on patient size and physician preference. The first retention balloon is selected to physically engage the bladder adjacent the bladder neck and to minimize migration of urine through the bladder neck and the anastomotic site. The retention balloon is preferably of a silicone material that is connected to the outer surface of the tubular member with commercially available medical grade adhesive. Prior to connection to the elongated tubular member, an access port is formed between first inflation passage 26 and external surface 35 of the tubular member. This access port provides communication between the inflation passage and the interior of the balloon for inflation and deflation thereof.

Second retention balloon 25 is positioned proximal to the drainage ports 21 and is connected to external surface 35 of the elongated tubular member in the same manner as first retention balloon 24. However, a separate access port is made in the external surface of the tubular member to provide communication between the interior of second balloon 25 and second inflation passage 27. Accordingly, the inflation passages provide for individual and independent inflation and deflation of the first and second retention balloons. Although the catheter has been described as having first and second inflation passages, only one inflation passage is needed to inflate both of the balloons. Second retention balloon 25 is also preferably of a silicone material and 30 cc in volume. However, the balloon can range in volume from 5–50 cc, again depending on patient size and physician preference. This second retention balloon is inflated to physically engage proximally against the dome of the patient's bladder and works in cooperation with first retention balloon 24 that physically engages distally against the base of the bladder about the bladder neck. This cooperation between the first and second retention balloons fixes the relative position of the drainage portion in the bladder and the distal portion in the urethra through the anastomotic site.

FIG. 3 depicts an enlarged, cross-sectional view of drainage portion 14 of drainage catheter 10 of FIG. 1 along the line 3—3. This cross-sectional view of elongated tubular member 11 of the catheter depicts drainage passage 12 with drainage port 16 extending through wall 36 of the elongated tubular member. As depicted in FIGS. 1 and 3, drainage port 16 is preferably elliptical in shape. A plurality of drainage ports 21 are positioned every centimeter along the length of the drainage portion. However, round or any polygonal drainage port is also contemplated.

By way of example, the overall length of the drainage catheter is approximately 65 cm and is uniformly 20 French (0.263") in diameter along its entire length, excluding the flared proximal end and the retention balloons. The preferred diameter is 20 French, however, the outside diameter of the catheter can range in size from 12 to 28 French. The distal portion 13 of the catheter is preferably 5 cm, but can range from as short as 1 cm or as long as need be to extend through the anastomotic site. This distal portion does not have any drainage ports and the distal end is closed. However, the length of the distal portion should be short enough to remain proximal to the fossa navicularis of the urethra without extending externally beyond the external urethral orifice. This is, again, to minimize the migration of pathogens and organisms or any other infectious material from reaching the anastomotic site.

The length of drainage portion 14 of the catheter between the first and second retention balloons is preferably 5 cm with a drainage port preferably every centimeter along its length. The length of the drainage portion can range from between 2 to 20 cm so that the first and second retention balloons maintain the drainage portion in the bladder and the distal portion in the urethra.

The material of the elongated tubular member is preferably silicone and, more preferably, a radiopaque silicone. However, it is contemplated that the drainage catheter can be made from any flexible, medical grade material such as latex or a polymeric material such as polyvinylchloride, with silicone or latex balloons attached as previously described. Furthermore, the material of the catheter can have a medicant embedded therein or attached thereto to prevent pathogens or organisms migrating to the anastomotic site or suprapubic access site. Rifampin/Minocycline is only one of a host of commercially available medicants that can be utilized. Surfactants, coatings, chemical bonding, implantation, embedding and encapsulation can be used singly or in combination to deliver one or more medicants at any desired delivery rate.

FIG. 4 depicts drainage catheter 10 of FIG. 1 suprapubically positioned in bladder 29 and urethra 19 through percutaneous access site 30. The catheter is placed suprapubically during and following excision of the prostate gland via open or laparoscopic surgery. This excision is commonly referred to as a radical prostatectomy in which the prostate gland is removed and the urethra 19 reconnected at anastomotic site 20. Distal portion 13 of the drainage catheter is positioned in urethra 19 through the anastomotic site. First retention balloon 24 is inflated to an expanded state to distally engage bladder neck 37. Drainage portion 14 of the catheter with drainage ports 21 is positioned in the bladder with second retention balloon 25 in an expanded state. Urine collected in the bladder enters drainage ports 21 and flows through the drainage passage of the catheter, out through proximal portion 15 and the connector hub of the catheter, and into a urine collection bag (not shown). As a result, the flow of urine into the urethra is minimized, if not eliminated, by the presence of first retention balloon 24 and the distal portion of the catheter in the urethra. Advantageously, the distal portion of the catheter also maintains patency of the urethra during healing of the urethra at anastomotic site 20.

A suprapubic catheter is preferable to the Foley catheter in that the Foley catheter would be transurethrally positioned and exit the urethra via external urethral orifice 38. The Foley catheter is undesirable in that the retention balloon can readily permit the flow of urine to the anastomotic site due to migration of the catheter. Secondly, placement of a Foley catheter through the external urethral orifice permits the migration of pathogens and organisms to the anastomotic site, which can significantly impede the healing process. Furthermore, the use of a Foley catheter is extremely uncomfortable to the patient, who experiences urges to pull the catheter out of the bladder. This unfortunately requires a reinsertion procedure, which significantly aggravates the healing process or even disrupts the anastomotic site.

It is to be understood that the above-described suprapubic drainage catheter is merely an illustrative embodiment of the principles of this invention and that other suprapubic drainage catheters can be devised by those skilled in the art without departing from the spirit and scope of this invention. In particular, it is contemplated that various previously-suggested materials can be utilized in the construction of the catheter, with or without a radiopaque filler, and that other expandable retention mechanisms, such as mechanical devices, can be utilized for the retention members. Although the elongated member is preferably tubular, the cross-sectional shape thereof can be elliptical, egg, bone, or any other shape to accommodate the anatomical shape of the urethra. Lastly, various sizes of the elongated tubular member of the catheter and its proximal, drainage, and distal portions can be fabricated to meet patient size and physician preference.

What is claimed is:

1. A drainage catheter for suprapubic drainage of a patient's bladder, said drainage catheter comprising:

an elongated member having a drainage passage extending longitudinally therein, at least one drainage port providing external access for said drainage passage, and a distal portion positioned distal of said at least one drainage port;

a first retention member connected with said elongated member and positioned distal of said least one drainage port;

a second retention member connected with said elongated member and positioned proximal of said at least one drainage port;

the distal portion extending at least one centimeter distal of said first retention member and otherwise sized and configured for maintaining patency of a vessel in a vicinity of an anastomotic site; and the distal portion being imperforate distal of said first retention member, thereby blocking external access of said drainage passage.

2. The drainage catheter of claim 1 wherein said elongated member also has a proximal portion positioned proximal of said at least one drainage port and providing external egress from the drainage passage, for drainage of fluids from said drainage passage.

3. The drainage catheter of claim 1 wherein said first and said second retention member includes a first and a second expandable member, respectively, each having a collapsed and an expanded state.

4. The drainage catheter of claim 1 wherein said first and said second retention member includes a first and a second balloon, respectively.

5. The drainage catheter of claim 4 wherein said elongated member includes at least one inflation passage extending longitudinally therein and communicating with said first and said second balloons.

6. The drainage catheter of claim 5 wherein said at least one inflation passage includes a first passage and a second passage communicating with said first balloon and said second balloon, respectively.

7. The drainage catheter of claim 1 wherein said distal portion includes an atraumatic end.

8. The drainage catheter of claim 1 wherein said at least one drainage port has an elliptical shape.

9. The drainage catheter of claim 1 wherein said elongated member includes a radiopaque material.

10. A drainage catheter comprising:

an elongated member having a drainage passage extending longitudinally therein, at least one drainage port providing external access for said drainage passage, and a distal portion positioned distal of said at least one drainage port;

a first retention member connected with said elongated member and positioned distal of said least one drainage port;

a second retention member connected with said elongated member and positioned proximal of said at least one drainage port;

the distal portion extending at least one centimeter distal of said first retention member and being imperforate distal of said first retention member, thereby blocking external access of said drainage passage; and said at least on drainage port includes a plurality of ports each providing external access for said drainage passage.

11. A drainage catheter comprising:

an elongated member having a drainage passage extending longitudinally therein, at least one drainage port providing external access for said drainage passage, and a distal portion;

a first retention member connected with said elongated member and positioned distal of said least one drainage port, said distal portion positioned distal of said first retention member;

a second retention member connected with said elongated member and positioned proximal of said at least one drainage port, said elongated member also having a proximal portion positioned proximal of said second retention member and providing external egress from the drainage passage, for drainage of fluids from said drainage passage; and the distal portion extending at least one centimeter distal of said first retention member and being imperforate distal of said first retention member, thereby blocking external access of said drainage passage.

12. The drainage catheter of claim 11 wherein said first and said second retention member includes a first and a second balloon, respectively.

13. The drainage catheter of claim 12 wherein said elongated member includes at least one inflation passage extending longitudinally therein and communicating with said first and said second balloons.

14. The drainage catheter of claim 13 wherein said at least one inflation passage includes a first passage and a second passage communicating with said first balloon and said second balloon, respectively.

15. The drainage catheter of claim 11 wherein said distal portion includes an atraumatic end.

16. A drainage catheter comprising:

an elongated member having a drainage passage extending longitudinally therein, at least one drainage port providing external access for said drainage passage, and a distal portion;

a first retention member connected with said elongated member and positioned distal of said least one drainage port, said distal portion positioned distal of said first retention member;

a second retention member connected with said elongated member and positioned proximal of said at least one drainage port, said elongated member also having a proximal portion positioned proximal of said second retention member and providing external egress from the drainage passage, for removal of fluids from said drainage passage;

the distal portion being imperforate distal of said first retention member, thereby blocking external access of said drainage passage, and said distal portion extending at least one centimeter distal of said first retention member and otherwise sized and configured for maintaining patency of a vessel only in the vicinity of an anastomotic site.

17. A drainage catheter comprising:

an elongated member having a drainage passage extending longitudinally therein, at least one drainage port providing external access for said drainage passage, and a distal portion;

a first retention member connected with said elongated member and positioned distal of said least one drainage port, said distal portion positioned distal of said first retention member;

a second retention member connected with said elongated member and positioned proximal of said at least one drainage port, said elongated member also having a proximal portion positioned proximal of said second retention member and providing external egress from the drainage passage, for removal of fluids from said drainage passage;

the distal portion extending at least one centimeter distal of said first retention member and being imperforate distal of said first retention member, thereby blocking external access of said drainage passage; and said at least one drainage port includes a plurality of ports each providing external access for said drainage passage.

18. A drainage catheter comprising:

an elongated member having a drainage passage extending longitudinally therein, at least one drainage port providing external access for said drainage passage, and a distal portion positioned distal of said at least one drainage port;

a first retention member connected with said elongated member and positioned distal of said least one drainage port;

a second retention member connected with said elongated member and positioned proximal of said at least one drainage port;

the distal portion extending at least one centimeter distal of said first retention member and being imperforate distal of said first retention member, thereby blocking external access of said drainage passage; and said drainage passage has a crescent, cross-sectional shape.

19. A drainage catheter comprising:

an elongated member having a drainage passage and a first and a second inflation passage extending longitudinally therein, a drainage portion having a plurality of drainage ports each providing external access for said drainage passage, a distal portion positioned distal of said plurality of drainage ports and sized and configured for maintaining patency of a vessel in a vicinity of an anastomotic site; and a proximal portion positioned proximal of said plurality of drainage ports and providing external access for said drainage passage;

a first balloon connected with said elongated member and positioned distal of said plurality of drainage ports, said first inflation passage communicating with said first balloon;

a second balloon connected with said elongated member and positioned proximal of said plurality of drainage ports, said second inflation passage communicating with said second balloon; and the distal portion extending at least one centimeter distal of said first retention member and being imperforate distal of said first balloon, thereby blocking external access of said drainage passage.

* * * * *